(12) United States Patent
Dominik et al.

(10) Patent No.: US 8,945,129 B2
(45) Date of Patent: Feb. 3, 2015

(54) FIXATION CLAMP WITH THUMBWHEEL

(75) Inventors: Robert Dominik, Lausanne (CH);
Adam Busch, Olten (CH); Klaus Dorawa, Safnern (CH)

(73) Assignee: Stryker Trauma SA (CH)

( * ) Notice: Subject to any disclaimer, the term of this patent is extended or adjusted under 35 U.S.C. 154(b) by 223 days.

(21) Appl. No.: 13/302,619

(22) Filed: Nov. 22, 2011

(65) Prior Publication Data
US 2012/0150182 A1 Jun. 14, 2012

(30) Foreign Application Priority Data

Dec. 14, 2010 (EP) .................................... 10194944

(51) Int. Cl.
| | | |
|---|---|---|
| *A61B 17/00* | (2006.01) | |
| *A61B 17/60* | (2006.01) | |
| *A61B 17/64* | (2006.01) | |
| A61B 17/86 | (2006.01) | |
| A61B 17/88 | (2006.01) | |
| A61B 19/00 | (2006.01) | |

(52) U.S. Cl.
CPC .............. *A61B 17/60* (2013.01); *A61B 17/6466* (2013.01); *A61B 17/6416* (2013.01); *A61B 17/645* (2013.01); *A61B 17/6458* (2013.01); *A61B 17/8615* (2013.01); *A61B 17/888* (2013.01); *A61B 2017/0023* (2013.01); *A61B 2019/4873* (2013.01)
USPC .............................................. 606/59; 606/54

(58) Field of Classification Search
USPC ......... 606/301–321, 104, 916, 54–59; 81/471
See application file for complete search history.

(56) References Cited

U.S. PATENT DOCUMENTS

| | | | | |
|---|---|---|---|---|
| 2,250,417 | A | | 7/1941 | Ettinger |
| 3,604,487 | A | * | 9/1971 | Gilbert ........................... 81/443 |
| D228,970 | S | | 10/1973 | Cohen |

(Continued)

FOREIGN PATENT DOCUMENTS

| | | |
|---|---|---|
| CA | 2121085 A1 | 10/1994 |
| CH | 657899 A5 | 9/1986 |

(Continued)

OTHER PUBLICATIONS

European Search Report for EP 10194943.6 dated Feb. 23, 2011.

(Continued)

*Primary Examiner* — Jan Christopher Merene
(74) *Attorney, Agent, or Firm* — Lerner, David, Littenberg, Krumholz & Mentlik, LLP

(57) ABSTRACT

A fixation clamp, more particularly for use in an external fixation system for holding bone fragments adjacent to each other with the help of fixation elements, has at least one clamping assembly having at least one reception opening to accommodate a fixation element along the longitudinal axis of the reception opening. At least one locking element extends through the clamping assembly which locking element provides a clamping force to clamp the fixation element upon tensioning the locking element. The fixation clamp further comprises an actuation element which is in connection with the locking element such that the locking element is actuateable by means of the actuation element, and the actuation element is designed such that it is detachable from the locking element after use and that remounting onto the locking element is prevented after having detached the actuation element from the locking element.

28 Claims, 9 Drawing Sheets

(56) References Cited

U.S. PATENT DOCUMENTS

| | | | |
|---|---|---|---|
| D237,631 S | 11/1975 | Katzman | |
| 3,985,170 A * | 10/1976 | Iskra | 81/438 |
| D255,713 S | 7/1980 | Sturges | |
| D282,962 S | 3/1986 | Gerber | |
| D283,725 S | 5/1986 | Mahoney | |
| 4,620,533 A | 11/1986 | Mears | |
| 4,662,365 A | 5/1987 | Gotzen et al. | |
| D301,496 S | 6/1989 | Yonesawa et al. | |
| 5,071,437 A | 12/1991 | Steffee | |
| 5,098,432 A | 3/1992 | Wagenknecht | |
| 5,152,280 A | 10/1992 | Danieli | |
| 5,304,177 A | 4/1994 | Pennig | |
| 5,376,091 A | 12/1994 | Hotchkiss et al. | |
| 5,429,637 A | 7/1995 | Hardy | |
| 5,443,465 A | 8/1995 | Pennig | |
| 5,630,815 A | 5/1997 | Pohl et al. | |
| D380,262 S | 6/1997 | Van Funderburk et al. | |
| 5,649,931 A * | 7/1997 | Bryant et al. | 606/104 |
| 5,662,648 A | 9/1997 | Faccioli et al. | |
| 5,746,741 A | 5/1998 | Kraus et al. | |
| 5,752,954 A * | 5/1998 | Mata et al. | 606/59 |
| 5,827,282 A | 10/1998 | Pennig | |
| 5,846,245 A | 12/1998 | McCarthy et al. | |
| 5,891,144 A | 4/1999 | Mata et al. | |
| 5,921,985 A | 7/1999 | Ross, Jr. et al. | |
| 6,019,769 A | 2/2000 | McCarthy et al. | |
| 6,024,745 A | 2/2000 | Faccioli et al. | |
| 6,080,153 A | 6/2000 | Mata et al. | |
| D429,334 S | 8/2000 | Solem | |
| 6,217,577 B1 | 4/2001 | Hofmann | |
| 6,308,598 B1 * | 10/2001 | O'Neil | 81/467 |
| D455,831 S | 4/2002 | Koros et al. | |
| 6,386,786 B1 | 5/2002 | Perlman et al. | |
| 6,409,729 B1 | 6/2002 | Martinelli et al. | |
| 6,482,206 B2 | 11/2002 | Schoenefeld | |
| 6,520,962 B1 | 2/2003 | Taylor et al. | |
| 6,565,564 B2 | 5/2003 | Hoffman et al. | |
| 6,613,049 B2 | 9/2003 | Winquist et al. | |
| 6,616,664 B2 | 9/2003 | Walulik et al. | |
| 6,652,523 B1 | 11/2003 | Evrard et al. | |
| D483,642 S | 12/2003 | Lin | |
| 6,702,814 B2 | 3/2004 | Walulik et al. | |
| D493,225 S | 7/2004 | Varga et al. | |
| D494,274 S | 8/2004 | Varga et al. | |
| D501,555 S | 2/2005 | Varga et al. | |
| 6,857,343 B1 * | 2/2005 | Easterbrooks et al. | 81/452 |
| 6,916,319 B2 | 7/2005 | Munting | |
| 7,004,943 B2 | 2/2006 | Ferrante et al. | |
| 7,048,735 B2 | 5/2006 | Ferrante et al. | |
| D526,410 S | 8/2006 | Phillips et al. | |
| D532,277 S | 11/2006 | Shih | |
| D537,939 S | 3/2007 | Phillips et al. | |
| 7,261,713 B2 | 8/2007 | Langmaid et al. | |
| D551,763 S | 9/2007 | Phillips et al. | |
| 7,282,052 B2 | 10/2007 | Mullaney | |
| D556,899 S | 12/2007 | Veliss et al. | |
| D558,337 S | 12/2007 | Jones et al. | |
| 7,449,023 B2 | 11/2008 | Walulik et al. | |
| 7,479,142 B2 | 1/2009 | Weiner et al. | |
| 7,491,008 B2 | 2/2009 | Thomke et al. | |
| 7,527,626 B2 | 5/2009 | Lutz et al. | |
| 7,562,855 B2 | 7/2009 | Oetlinger | |
| 7,588,571 B2 | 9/2009 | Olsen | |
| 7,618,417 B2 | 11/2009 | Thomke et al. | |
| D607,102 S | 12/2009 | Robinson | |
| 7,749,224 B2 | 7/2010 | Cresina et al. | |
| 7,806,623 B2 | 10/2010 | Thomke et al. | |
| D632,791 S | 2/2011 | Murner | |
| D633,206 S | 2/2011 | M rner | |
| D633,207 S | 2/2011 | Murner | |
| D633,208 S | 2/2011 | Murner | |
| 8,172,840 B2 | 5/2012 | Murner et al. | |
| D663,030 S | 7/2012 | Murner et al. | |
| 8,343,166 B2 | 1/2013 | Maughan et al. | |
| 8,382,804 B2 | 2/2013 | Thomke et al. | |
| 8,523,858 B2 | 9/2013 | Lessig et al. | |
| 2001/0049526 A1 | 12/2001 | Venturini et al. | |
| 2002/0037193 A1 | 3/2002 | Gibbons et al. | |
| 2002/0077629 A1 | 6/2002 | Hoffman et al. | |
| 2002/0165543 A1 | 11/2002 | Winquist et al. | |
| 2003/0199738 A1 | 10/2003 | Yager | |
| 2004/0044344 A1 | 3/2004 | Winquist et al. | |
| 2004/0059331 A1 | 3/2004 | Mullaney | |
| 2005/0203520 A1 | 9/2005 | Volzow | |
| 2005/0240265 A1 | 10/2005 | Kuiper et al. | |
| 2006/0025703 A1 | 2/2006 | Miles et al. | |
| 2006/0039750 A1 | 2/2006 | Thomke et al. | |
| 2006/0052785 A1 | 3/2006 | Augostino et al. | |
| 2006/0155276 A1 | 7/2006 | Walulik et al. | |
| 2006/0167453 A1 | 7/2006 | Hoffmann-Clair et al. | |
| 2006/0217738 A1 * | 9/2006 | Tanimura | 606/104 |
| 2006/0287652 A1 | 12/2006 | Lessig et al. | |
| 2007/0038217 A1 | 2/2007 | Brown et al. | |
| 2007/0123856 A1 | 5/2007 | Deffenbaugh et al. | |
| 2007/0198012 A1 | 8/2007 | Thomke et al. | |
| 2007/0227314 A1 * | 10/2007 | Erickson et al. | 81/467 |
| 2007/0233061 A1 | 10/2007 | Lehmann et al. | |
| 2008/0065068 A1 | 3/2008 | Thomke et al. | |
| 2008/0215053 A1 | 9/2008 | Thomke et al. | |
| 2008/0269768 A1 * | 10/2008 | Schwager et al. | 606/104 |
| 2008/0306527 A1 | 12/2008 | Winslow et al. | |
| 2008/0306528 A1 | 12/2008 | Winslow et al. | |
| 2009/0018541 A1 | 1/2009 | Lavi | |
| 2009/0088751 A1 | 4/2009 | Mullaney | |
| 2009/0099565 A1 | 4/2009 | Weiner et al. | |
| 2009/0299368 A1 | 12/2009 | Bauer | |
| 2009/0306661 A1 | 12/2009 | Thomke et al. | |
| 2009/0326532 A1 | 12/2009 | Schulze | |
| 2010/0298827 A1 | 11/2010 | Cremer et al. | |
| 2011/0066151 A1 | 3/2011 | Murner et al. | |
| 2011/0087226 A1 | 4/2011 | Murner et al. | |
| 2012/0004659 A1 | 1/2012 | Miller et al. | |
| 2012/0150181 A1 | 6/2012 | Dorawa et al. | |
| 2012/0150183 A1 | 6/2012 | Dorawa et al. | |

FOREIGN PATENT DOCUMENTS

| | | |
|---|---|---|
| DE | 518329 C | 2/1931 |
| DE | 10246418 A1 | 4/2004 |
| EP | 314021 A2 | 5/1989 |
| EP | 0700664 A1 | 3/1996 |
| EP | 2250968 A1 | 11/2010 |
| FR | 2787697 A1 | 6/2000 |
| JP | 2003325058 A | 11/2003 |
| WO | 0156486 A1 | 8/2001 |
| WO | 2006116307 | 11/2006 |
| WO | 2007001945 A1 | 1/2007 |

OTHER PUBLICATIONS

European Search report for EP 10194944.4 dated Feb. 23, 2011.
European Search Report for EP 10194945.1 dated Feb. 25, 2011.
http://emedicine.medscape.com/article/1982756-overview searched RMS Jan. 15, 2013.
http://www.smith-nephew.com/us/professional/products/all-products/jet-x/ searched RMS Jan. 15, 2013.

* cited by examiner

FIXATION CLAMP WITH THUMBWHEEL

CROSS-REFERENCE TO RELATED APPLICATION

The present application claims priority from European Patent Application No. 10 194 944.4 filed Dec. 14, 2010, the disclosure of which is hereby incorporated herein by reference.

BACKGROUND OF THE INVENTION

The present invention relates to a fixation clamp and, more particularly, to a fixation clamp for use in an external fixation system for holding bone fragments adjacent to each other.

External fixation systems are widely used to connect two or more bone fragments to each other. Such systems comprise bone screws, pins, wires which are inserted directly into the bone material and these systems use external structural elements as fixation rods, bars and rings. In order to connect the rods and bars to form a rigid frame, fixation clamps are used. Furthermore, fixation clamps are used to connect this screws and pins to the rigid frame to specifically hold bone fragments at an intended place.

One adjustable fixation clamp is known from U.S. Pat. No. 6,080,153 comprising two pairs of jaws allowing clamping of a rod as well as of a pin.

A clamp for multiple rod-shaped elements is known from U.S. Pat. No. 7,618,417 having one single pair of jaws. However, such a clamp allows clamping more than two, e.g. three or four rod-shaped elements as pins with one single clamp, thus reducing the number of clamps. However, one further fixation clamp is necessary to fix the rod of said clamp to the frame of the fixation system.

U.S. Patent Application Publication No. 2006/0287652 mentions that usual fixation clamps as e.g. known from U.S. Pat. No. 6,080,153 allow clamping of one single screw or pin to the frame and that this way to attach pins or rods leads to bulky fixation systems. Therefore U.S. Patent Application Publication No. 2006/0287652 discloses a fixation clamp addressing this problem and comprises two pairs of jaws within which each pair of jaws allows the introduction and clamping of two rods or pins etc. at the same time.

These clamps according to the prior art either provide different diameters of the receptions provided by the jaws to introduce different sizes of rods, pins or wires, or they rely on additional inserts as e.g. disclosed in U.S. Patent Application Publication No. 2008/065068. Such inserts reduce the diameter of the reception cavities to allow a secure fixing of differently sized rods, pins or wires.

From U.S. Patent Application Publication No. 2010/0298827 a further fixation clamp is known. Although the users such as surgeons provide very good feedback concerning the handling of such a fixation clamp, many of the users mentioned clamping process in some occasions is difficult.

Furthermore the fixation clamps as known from prior art have the drawback that the user is not able to recognize, if the fixation clamp has been sterilized or if it was already used.

BRIEF SUMMARY OF THE INVENTION

It is an aspect of the present invention to provide a fixation clamp which provides an easier clamping process, in particular the fixation clamp shall be pre-tensioned manually or hand-operated respectively, and tensioned by means of a tool, such as a wrench.

Such an aspect is solved by the features of claim 1. Accordingly a fixation clamp, more particularly for use in an external fixation system for holding bone fragments adjacent to each other with the help of fixation elements, comprises at least one clamping assembly having at least one reception to accommodate a fixation element along the longitudinal axis of the reception and at least one locking element extending through the clamping assembly which locking element provides a clamping force to clamp the fixation element upon tensioning the locking element. The fixation clamp comprises an actuation element which is in connection with the locking element such that the locking element is actuateable by means of the actuation element, and the actuation element is designed such that it is detachable from the locking element after use and that remounting onto the locking element is prevented after having detached the actuation element from the locking element.

By means of the actuation element the locking element can be pre-tensioned or pre-tightened. After removal of the actuation element a conventional tool can be use to tighten the locking element firmly. Since the actuation element is provided such that it is not remountable once it has been detached from the locking element, the user is able to separate used or non-used fixation clamps.

Preferably the actuation element is designed as single-use or disposable element.

Preferably the actuation element is provided with at least one latching element which engages with the locking element. Alternatively the actuation element comprises at least two or at least three latching elements which are arranged diagonally with respect to the locking element from each other. Thereby the latching elements are arranged such that it is not possible to spread the latching element by means of a tool such as a screwdriver which means that with such a configuration the risk that the user remounts the actuation element becomes even smaller.

Further embodiments of the invention are set forth in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
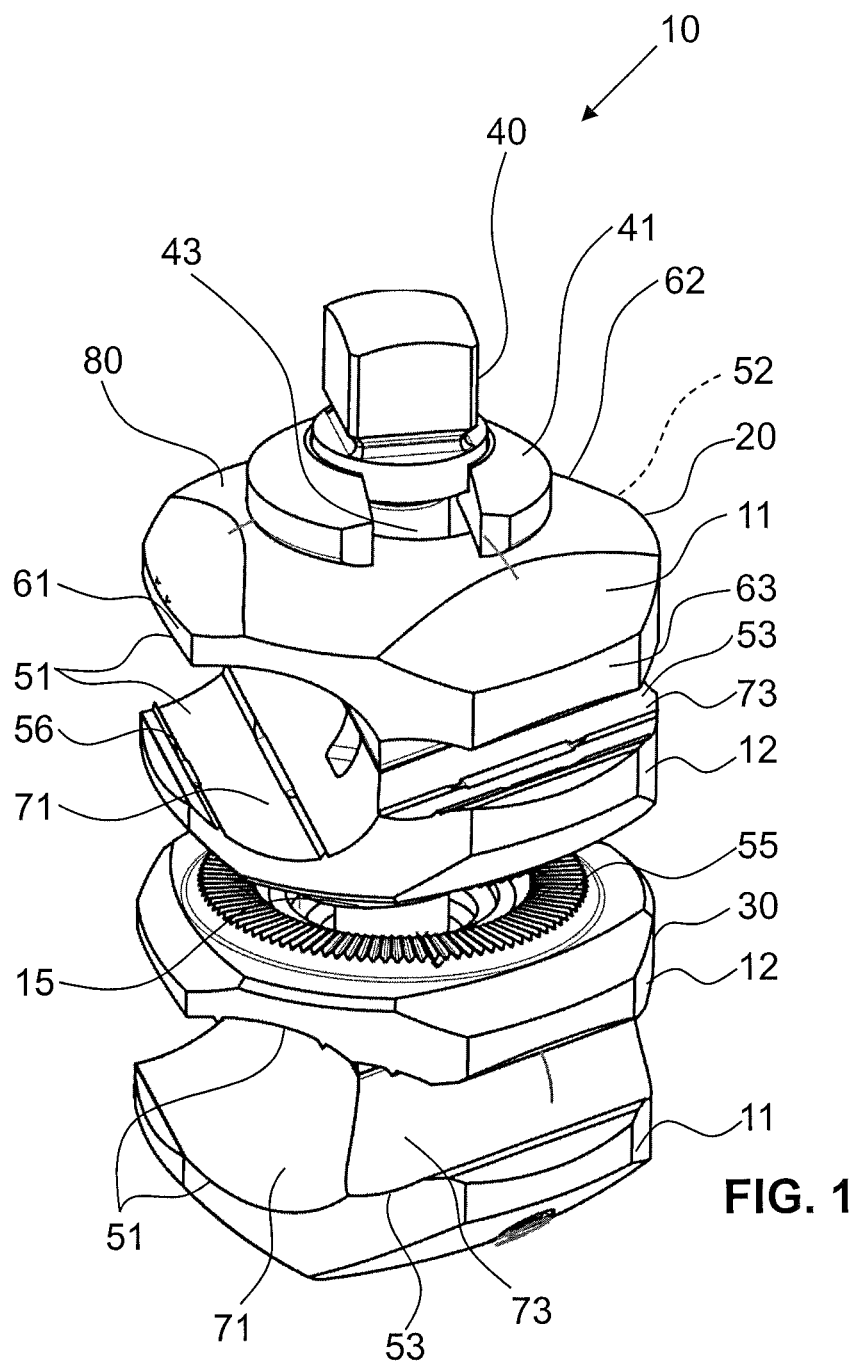
FIG. 1 shows a perspective view of a first embodiment of a fixation clamp of the present invention.
Figure 2:
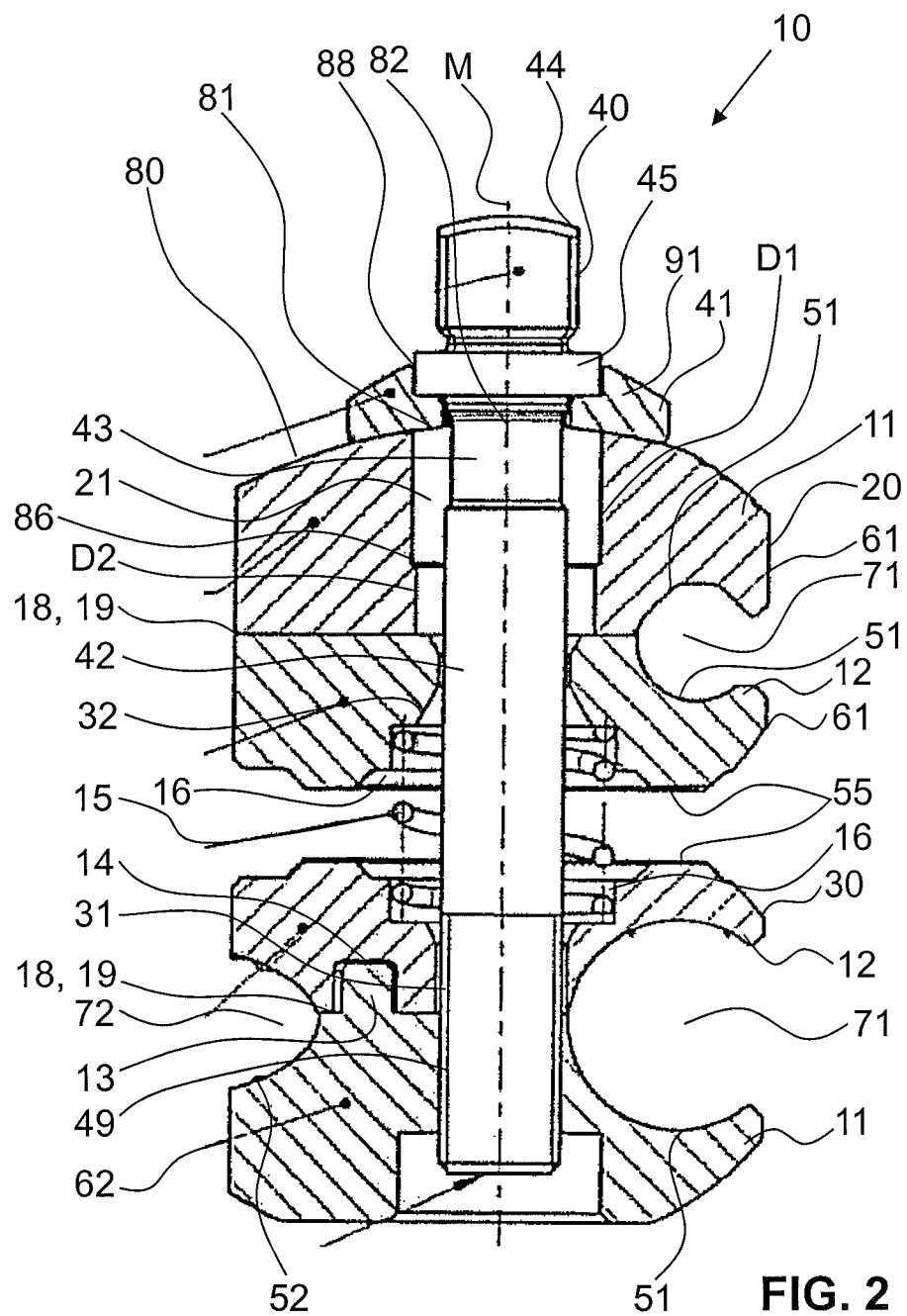
FIG. 2 shows a cross-section of the fixation clamp according to FIG. 1.

FIGS. 1 and 2 show a preferred first embodiment of a clamping element or fixation clamp 10 pursuant to the invention. The clamping element 10 consists of a first clamping assembly 20 and a second clamping assembly 30 and a locking element or shaft 40 which is positioned through bores 21, 31 within the two clamp assemblies 20, 30 along the longitudinal axis M of shaft 40. The shaft 40 is preferably a locking element adapted to allow closing the clamp assemblies 20 and 30. Shaft 40 enters a first jaw 11 through a washer 41.

The shaft 40 comprises a head portion 44, a reduced diameter portion 43 which is followed by a shaft portion 42 and a thread portion 49. The outer threaded portion 49 is adapted to be screwed into a complementary inner thread within the distal jaw 11 so that turning the head of the shaft 40 changes the longitudinal position of the shaft 40 against the lower jaw 11, which allows opening or closing the entire clamp 10 against the force of a spring 15 provided between the two clamp assemblies 20 and 30. Spring 15 is preferably positioned in corresponding receptions 16 in the jaws 12. Instead of a spring 15, provided around shaft 40, it is possible to provide a different spring means as Belleville washers or an elastic compressible solid or foam. Upon closing of the clamp assemblies 20 and 30 the jaws 12 adjacent to the spring 15 can eventually come into contact and then the anti-rotation surfaced 55 which are provided in both surfaces of the jaws 12 to fix the angular orientation of each clamping assembly 20 and 30 against the other.

Preferably after having mounted the shaft 40 with the thread 49 within the lower jaw 11, the end portion of the thread 49 is destroyed through pressure and deformation to ensure that the shaft 40 cannot be removed from the clamping assemblies 20, 30 to maintain the clamp as one single piece.

Each clamping assembly 20 or 30 comprises two opposing clamping jaws 11 and 12. These jaws 11 and 12 are essentially similarly shaped on the sides facing each other. Each of the jaws 12, 11 comprises a respective contact surface 18, 19 facing the other surface of the jaw 11, 12.

In order to prevent rotation between the jaw 11 and the jaw 12 as well as in order to prevent a misalignment of the jaw 11, 12 at least one orientation device 13, 14 is arranged on the surfaces 18, 19. In the present embodiment in the second clamping assembly 30 the jaw 11 comprises an opening 14 such as a counterbone extending into surface 18 and the jaw 12 comprises a pin 13 extending from surface 19. The pin 13 extends into the opening 14. This pin-opening connection prevents therefore a possible rotation between the jaws 11, 12 and a possible misalignment between the jaws 11, 12.

The jaws 11 and 12 are provided here with three grooves 51, 52 and 53. Grooves 51, 52 and 53 are all provided in a same plane perpendicular to the longitudinal axis of shaft 40. In that plane they are oriented perpendicular to the radial direction from the center of the bore 21 or 31. As such the grooves 51, 52 and 53 are substantially parallel to outer side wall 61, 62 or 63 of each pair of jaws 11 and 12.

Each pair of grooves 51, 52 or 53, respectively, in each jaw 11 and 12, define one recess or reception, i.e., a first reception 71, a second reception 72 and a third reception 73. The grooves 51, 52 and 53 are each formed as a rounded semi-spherical recess in section to provide receptions 71, 72 and 73 which accommodate cylindrical pins or rods with a defined diameter, if the clamp is closed. The outer side walls 61, 62 or 63 can comprise an inclined sliding surface to allow an easier clipping of such pins or rods 100 into the corresponding reception. The grooves 51, 52, 53 are called to form rounded semi-spherical recesses in a section. This means that the recesses provided by the grooves 51, 52, 53 have a hollow cylindrical shape to accommodate rod-shaped elements. Some or all of the grooves 51, 52, and 53 are also provided with friction enhancing elements such as ribs 56.

All three grooves 51, 52 and 53 have different sizes so that the corresponding receptions 71, 72 and 73 have three different sizes. In other words each reception 71, 72 or 73 is adapted to accept a different fixation element, i.e. a rod, screw, pin or wire having a different diameter. One preferred embodiment of the first clamping assembly 20 has grooves to accept fixation elements having a diameter of 12 mm, 8 mm and 5 mm, respectively. A different embodiment may have a sequence of diameters of 8 mm, 6 mm and 4 mm, respectively.

The second clamping assembly 30 according to the embodiment of FIG. 1 also comprises two jaw portions 11 and 12 and these comprise three grooves 51, 52, 53. These grooves 51, 52, 53 also comprise a sequence of different sizes. In the embodiment shown the inner jaws portion 12 have an identical structure as have the outer jaws 11, especially in view of the anti-rotation device 55, the reception 16 for a spring 15.

Within a preferred embodiment the first clamping assembly 20 may comprise a sequence of smaller sizes, e.g. 7 mm, 5 mm and 3 mm; or 6 mm, 5 mm and 4 mm; and the second clamping assembly 30 may comprise a sequence of larger sizes, e.g. 13.5 mm, 12 mm and 10 mm. Different sizes are possible, usually for wires starting from 2 mm diameter until thicker rods with a diameter of 30 mm are used within such a clamp 10. Such a clamp allows using one single versatile clamp, wherein the first clamping assembly 20 is used to fix a specific pin or screw or wire having a diameter for which one of the receptions 71, 72 or 73 is adapted. The user takes the clamp 10 and orients the first clamping assembly 20 into the correct alignment so that the pin or screw can be clipped into the corresponding reception.

Then the clamp 10 can be clamped on a rod of an external fixator with the help of the second clamping assembly 30. Second clamping assembly 30 can be oriented in a way so that the rod can be clipped into the corresponding reception. It is an advantage of the clamp 10 having two clamping assemblies 20 and 30 according to the invention, that a practitioner attaching such a clamp at a bone screw with one clamping assembly 20 and subsequently a rod of an external fixator to the other clamping assembly 30 can check the robustness of his external fixator, and if he finds that the rod he has used is not stiff enough, he simply opens the second clamping assembly 30, removes the thinner rod, turns the second clamping assembly 30 e.g. 60 degrees into one direction or the other around the longitudinal axis to align the larger reception with the new thicker rod and replaces it. This change does not necessitate the replacement of the clamp 10 itself as necessary with prior art systems. The method to replace such a rod is faster and more reliable since the clamping of the bone screw is not changed, and avoids use of a second sterile clamp at said time.

It is of course also possible that the second clamping assembly 30 is a traditional clamping assembly or even any other element known in the prior art with clamping elements. The object of a versatile clamping assembly is already achieved through one first clamping assembly 20, since it allows clamping one of three different sizes of screws, pins of wires through simple reorientation of the first clamping assembly 20.

FIG. 2 shows a cross-section of the clamp according to FIG. 1, wherein the clamp 10 is shown in a premounted or preassembled state, i.e. the spring 15 is under tension. The upper jaw 11 of the first clamping assembly 20 is therefore pushing the washer 41 against a flange 45 of the head of shaft 40. The bore 21 which accommodates part of the shaft portion 42 and the reduced diameter portion 43 is provided with a larger diameter than the respective diameter of the shaft 40 so that an angular or pivoting movement of the first clamping assembly 20 against the shaft 40 is possible. This is in particularly advantageous during the mounting process of the fixation clamp. In this regard it has to be noted that also bore 31 can be provided with a larger diameter than the respective section of the shaft 40 such that jaw 12 of the second clamping assembly becomes pivotable to the shaft 40.

The diameter D1, D2 of bore 21 of the first clamping assembly 20 is larger than the diameter of the locking element 40 extending through the bore 21. Thereby a pivoting movement or displacement between the locking element 40 and the first clamping assembly 20 during positioning the clamping assemblies 20, 30 and the pins or rods becomes possible. In the present embodiment the bore 21 in the first jaw 11 is a bore 21 having an abutment surface 86. The abutment surface 86 is provided by means a step-like bore 21 having a first section with a first diameter D1 and a second section with a second diameter D2. The first diameter D1 is larger than the second diameter D2. The abutment surface 86 serves as abutment element for the locking element 40 in particular for the flange 45 in case washer 41 is removed. Hence the abutment surface 86 together with the flange prevents that the first clamping assembly 20 will be separated from the second clamping assembly 30 when the washer is removed. Particularly during a cleaning or sterilization process the prevention of such a separation is very advantageous.

Alternatively the bore 21 can be provided with a conical section 32 as shown with bore 21 in the jaw 12 of the first clamping assembly. In the present embodiment there are two conical sections arranged, whereby the diameter of the bore 21 decreases with increasing length of the bore as seen from outside of the jaw 12. In case two conical sections 32 are present the degree of the pivoting motion can be increased.

The shaft 40 as part of a locking element is threaded into the lower jaw 11 of the second clamping assembly 30. Hence the lower jaw 11 comprises a threaded opening. Threading may be provided in the bore or the screw may exhibit self-tapping threading. Quite generally, a locking element may be provided which may be a lever locking element or a bayonet lock. Among these locking elements may also be supporting disks or toothed disks, which, for the sake of simplicity, are not shown in the drawings.

Therefore the two clamp assemblies 20, 30 can be opened and closed through turning the head of shaft 40 and thus turning shaft 40 in the jaw thread.

In the cross-sectional view of FIG. 2 it can also be seen that the locking element 40 extends through the first clamping assembly 20 and is in contact with the second clamping assembly 30 by means of the threaded portion 49. In mounting position in which the rods or pins will be positioned in the receptions 71, 72, 73 the first clamping assembly 20 is moveable along the middle axis M of the threaded portion 49. Upon actuation of the locking element 40 the first clamping assembly 20 will be moved against the spring pressure towards the second clamping assembly 30 such that the anti-rotation surface 55 of the first clamping assembly 20 comes into contact with the respective anti-rotation surface 55 of the second clamping assembly 30. Once the locking element 40 is firmly tightened the first clamping assembly 20 and the second clamping assembly 30 are in contact with each other via the anti-rotation surface 55.

In FIG. 2 the mounting position of clamping assemblies 20, 30 is shown. Thereby the clamping assemblies 20, 30 are positioned at the distance to each other with regard to the middle axis M. The second clamping assembly 20 is in contact with the locking element 40 and the spring 15 pushes the first clamping assembly away from the second clamping assembly 20 towards the washer 41 which is contact with the flange 45 of the locking element.

To summarize: The clamping assemblies 20, 30 will be moved due to actuation of the locking element 40 from a mounting position to a locking position and afterwards when fixation shall be cancelled from the locking position to the mounting position. After use the washer 41 will be removed as explained below in order to sterilize the clamping element 10 for further use.

Figure 3:
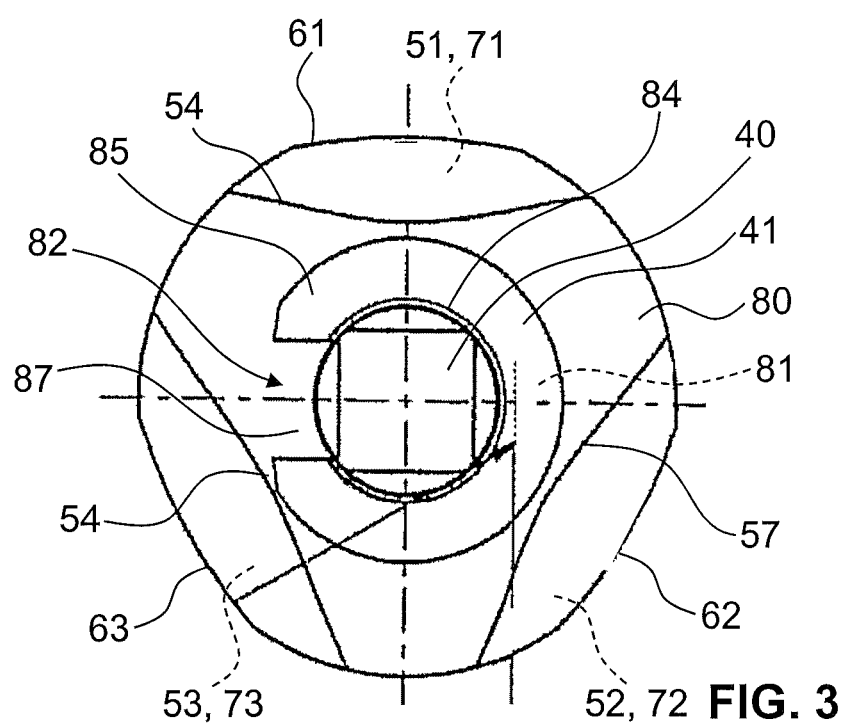
FIG. 3 shows a top view of the fixation clamp for FIG. 1.

FIG. 3 shows a view from above on the clamp according to FIGS. 1 and 2. Since the embodiment of FIG. 1 comprises three grooves 51, 52 and 53, there are three side walls 61, 62 and 63, which provide, when looked from above as in FIG. 2 a triangular shape of each clamping assembly 20 or 30.

The clamping element 10 further comprises an actuation element 90 or thumbwheel which is used to pretighten the locking element 40 before it is tightened by means of a tool such as a wrench. Such an actuation element 90 is shown in FIGS. 4 to 11, whereby in those figures the fixation clamp according to FIGS. 1 and 3 is shown. For the sake of simplicity not all reference numerals regarding the fixation clamp 10 have been added.

Figure 4:
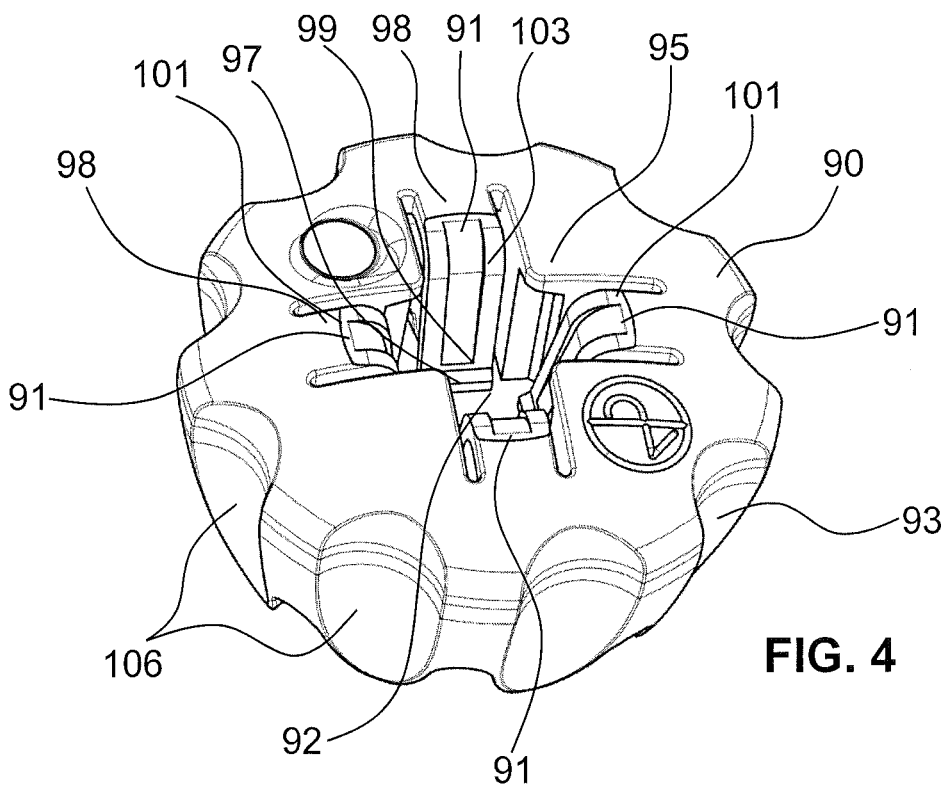
FIG. 4 shows a perspective view from the top of an actuation element which is connectable to the fixation clamp of FIG. 1.
Figure 5:
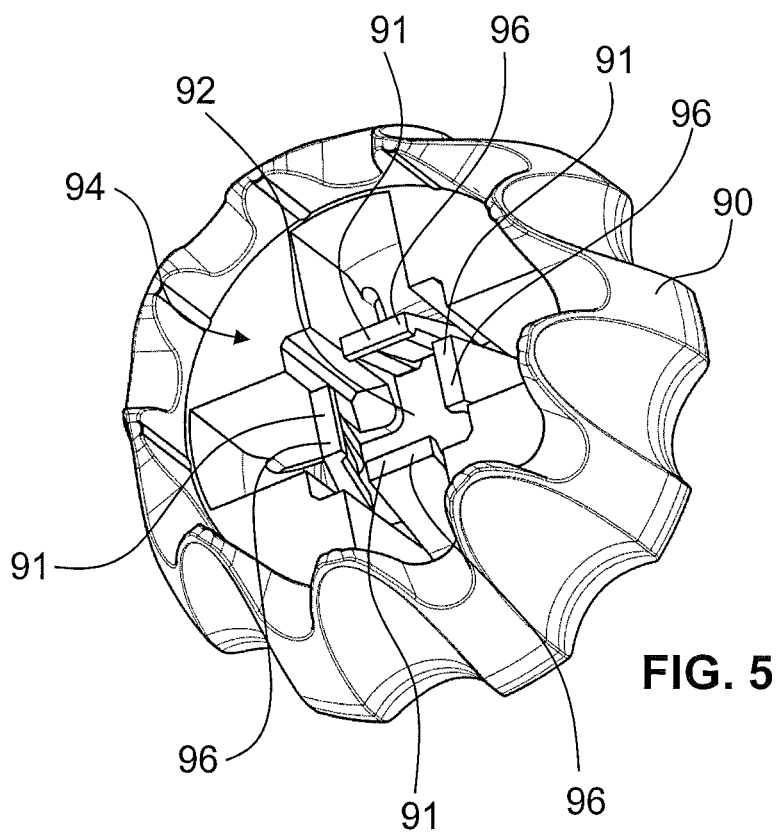
FIG. 5 shows a perspective view from the bottom of the actuation element of FIG. 4.
Figure 6:
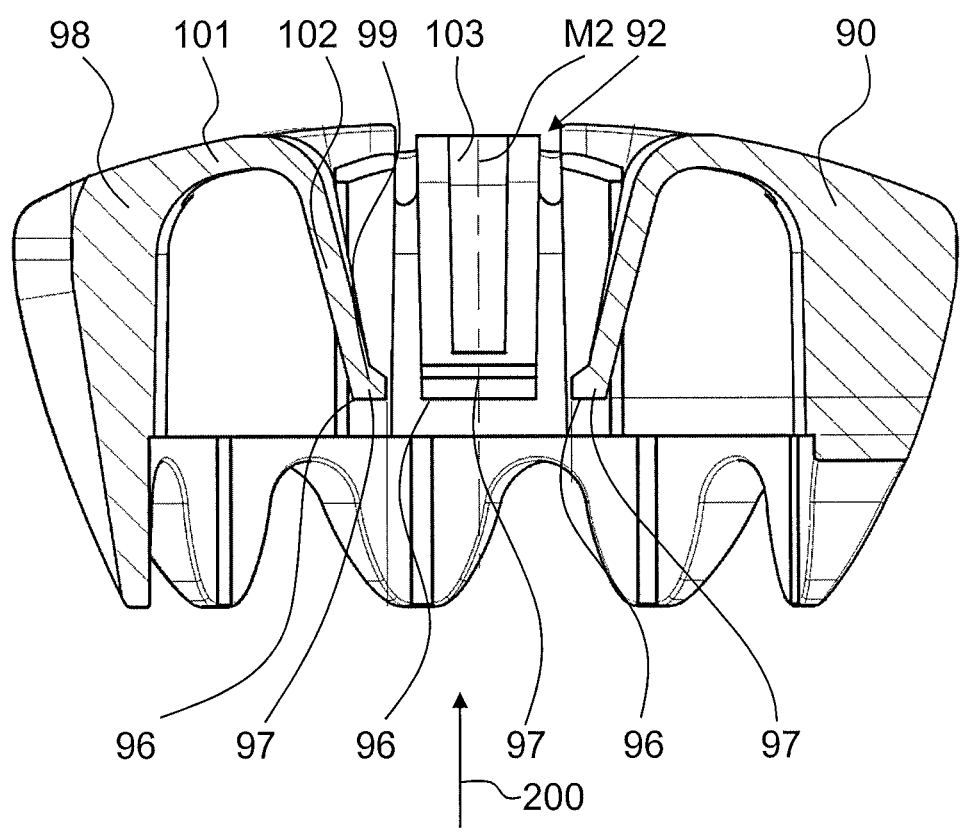
FIG. 6 shows a cross-sectional view of the actuation element of FIG. 4.

FIGS. 4 to 6 show views of an actuation element 90 to actuate the locking element 40 in order to pretighten the fixation clamp 10 by hand. The actuation element 90 is designed as single use element. Preferably the actuation element 90 is mounted onto the locking element 40 during or shortly after the process of sterilizing the fixation clamp 10. After pretightening the fixation clamp 10 the actuation element 90 is removed by the user, e.g. a surgeon or an assistant of the surgeon. The user then is able to tighten the locking element 40 by means of a tool that engages the head portion 44 of the locking element. Since the actuation element 90 is designed as single use element it is not possible to remount the actuation element 90 onto the locking element 40 after having it detached from the locking element 90. This has the advantage the one can easily recognize, if the fixation clamp 10 has already been used or if it is still ready to be used, e.g. if it is still sterilized.

To summarize: the actuation element 90 is designed such that it is mountable by means of a mounting tool 110 onto the locking element 40, that it is detachable from the locking element 40 after use and that remounting onto the locking element 40 is prevented after having detached the actuation element 90 from the locking element 40.

Hence the actuation element 90 is provided in mainly three states, namely in a mounting state in which the actuation element 90 is mounted onto the fixation clamp 10, in a mounted state in which the actuation element 90 is fixedly connected with the locking element 40 and in a detached state in which the actuation element 90 is detached from the locking element 10 and in which it is impossible to remount the actuation element 90. In the mounted state the fixation clamp 10 is ready for use in a surgery.

The actuation element 90 comprises in the present embodiment, a sidewall 93 which may be cylindrical or scalloped, a frontwall 95 extending substantially perpendicular to sidewall 93, a central opening 92 extending along a middle axis M2 substantially parallel to sidewall 93 and at least one, here four, latching elements 91. The sidewall 93 and the frontwall 95 encompass an interior space 94 in which the latching elements 91 extend. The latching elements 91 extend from the frontwall 95 in direction of middle axis M2 into said interior space 94 and are designed to engage with the locking element 40.

The latching elements 91 are provided as elastic or resilient deflectable beam elements having a first end 98 which is in contact with the sidewall 93 or the frontwall 95 and a second end 99 which is provided as loose or free end. In the present embodiment the first end 98 is in contact with or connected to with the frontwall 95 and the first end 98 extends over a first segment 101 substantially parallel to frontwall 95 and over a second segment 102 substantially perpendicular or angular to frontwall 95. Latching elements 91 are elastically deformable by means of a mounting tool 110 from a blocking position in which the locking element 40 is not insertable into the actuation element 90 to a mounting position in which the actuation element 90 is mounteable onto the locking 40.

The second end or loose end 99 is provided with an engaging element 97 which engages with the locking element 40. The engaging element 97 here has the shape of an embossment extending from the loose or free end 99 into the interior space 94.

Reference is made to the cross-sectional view of the actuation element 90 in FIG. 6. The actuation element 90 will be moved along its middle axis M1 with respect to the locking element 40. In the present embodiment the locking element 40 enters the interior space from below in FIG. 6 as indicated by arrow 200.

In the vicinity of each second end 99 there is arranged an abutment surface 96. The abutment surface 96 is arranged substantially perpendicular to middle axis M2 and extends into the central opening 92. In case the user tries to remount the actuation element 90 onto the locking element 40 the abutment surface 96 blocks the locking element 40 from intruding into the interior space 94. Hence the abutment surface 96 blocks a movement of the locking element 40 into the interior space 94 as it extends into the path of the locking element 40.

The latching element 91 in the present embodiment is provided with an optional guiding slot 103 which extends as seen from the central opening 92 or the middle axis M2 into the latching element 91. Guiding slot 103 serves to accommodate a respective counter part of the mounting tool 110.

The actuation element 90 comprises furthermore an outer surface on cylindrical sidewall 93 which outer surface comprises friction enhancing elements 100 in order to increase friction between a user's hand and the actuation element. In the present embodiment the friction enhancing elements 100 are hollow channels extending in direction of the middle axis M2 into sidewall 93. Furthermore the sidewall 93 comprises also recesses 104 extending into sidewall 93.

From FIGS. 1 and 2 it can be seen that the locking element 40 comprises in its head portion 44 adjacent to flange several recesses 46. In the present embodiment the head portion comprises several, here four side surfaces 48 extending from the flange 45 along middle axis M. The head portion 44 ends with a top surface 47 which is arranged substantially perpendicular to the middle axis M and to the side surfaces 48. The top surface 47 here is slightly convex. The side surfaces 48 serve as engaging surface for a tool in order to tighten the locking element 40. In the present embodiment the recesses 46 extend into the head portion 44, in particular into the side surfaces 48 of the locking element 40.

Figures 7, 8:
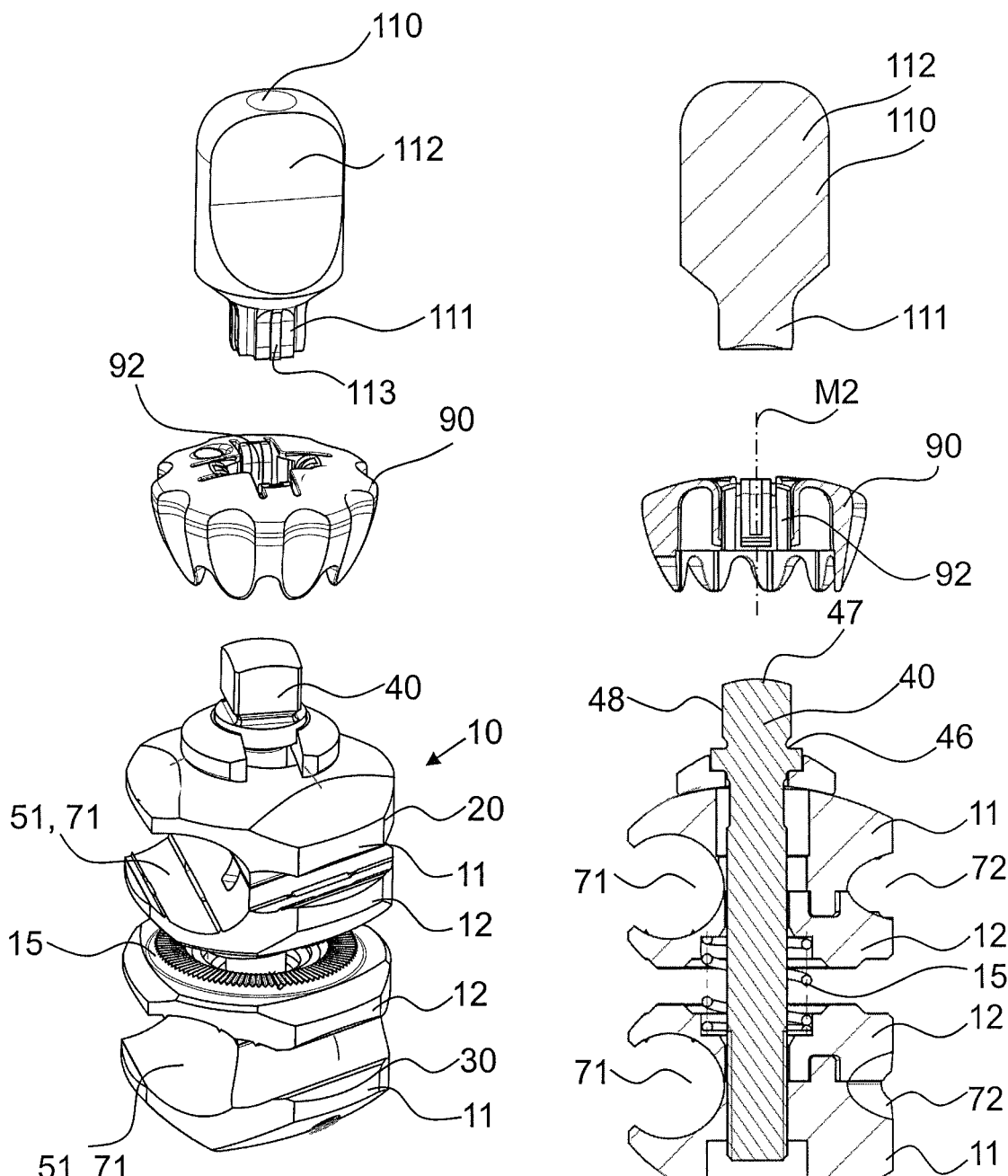
FIG. 7 shows a perspective view of the fixation clamp of FIG. 1 and the actuation element of FIG. 4 before mounting the actuation element onto the fixation clamp.
FIG. 8 shows a cross-sectional view of FIG. 7.

Reference is now made to FIGS. 7 and 8 in which the actuation element 90 is shown above the fixation clamp 10. Furthermore a mounting tool 110 to mount the actuation element 90 onto the fixation clamp 10 is shown. The mounting tool 110 is used to mount the actuation element 90 onto the locking element during or shortly after sterilizing the fixation clamp 10. The mounting tool 110 mainly serves to push the latching element away from the middle axis M2 so that the clearance between the latching elements 91 becomes larger in order to receive the head portion 44 of the locking element 40. With other words it can also be said that the abutment surfaces 96 will be moved away from the middle axis M2 such that they give way for the head portion 44.

The mounting tool 110 comprises a tool section 111 and a handle section 112. The tool section 111 is provided such that the mounting tool 110 can be inserted into the central opening 92 and pushes the latching elements 91 away from the middle axis M2 in order to enlarge the clearance between the latching elements 91. In case the latching elements 91 are provided with the guiding slots 103 the tool section 111 comprises a respective embossment 113 that is adapted to engage into the guiding slot 103. The handle section 112 is provided such that it can be grasped by a hand of a mounting person.

Figure 9:
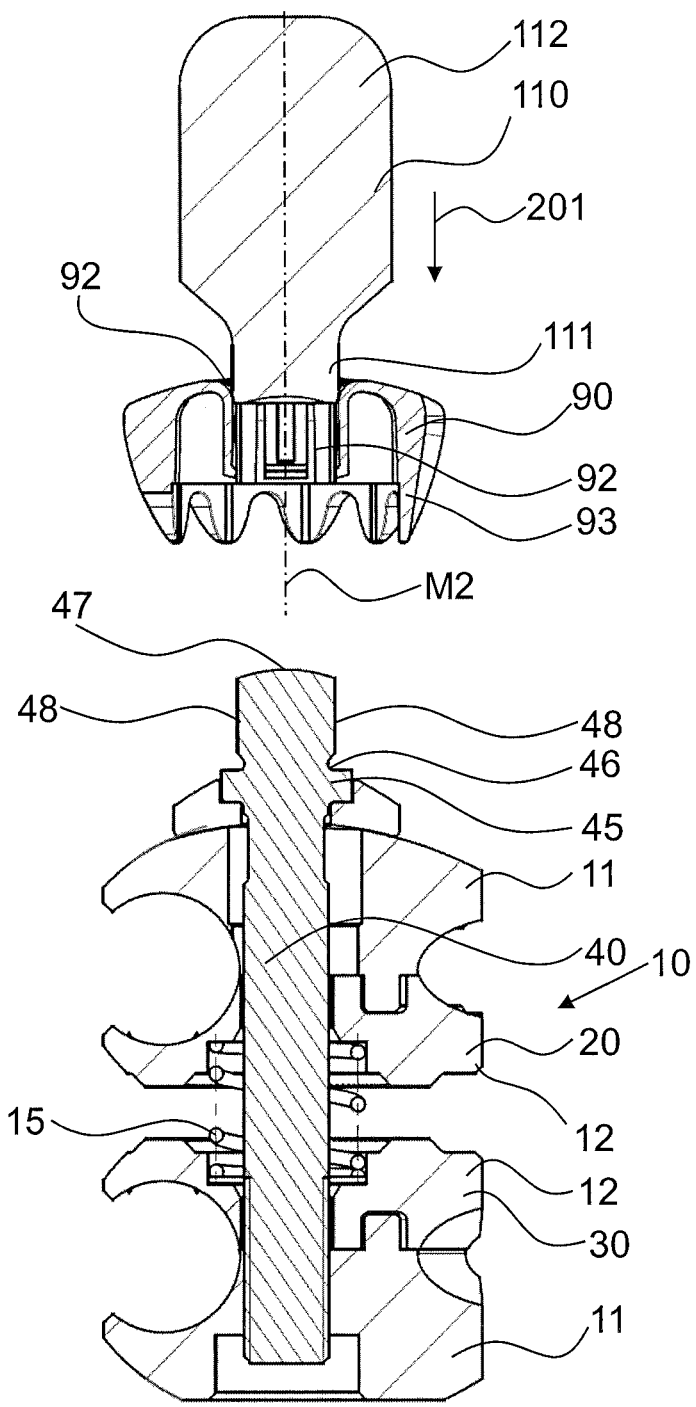
FIG. 9 shows a cross-sectional view of the arrangement of FIG. 7 in a pre-assembled state.

In FIG. 9 it is shown that the mounting tool 110 will be inserted with the tool section 111 into the central opening 92. This is shown by arrow 201. Thereby the latching elements 91 will be moved away from the middle axis M2. Hence the abutment surfaces 96 as well as the engaging elements 97 will be moved away from the middle axis M2 towards the sidewall 93.

Figure 10:
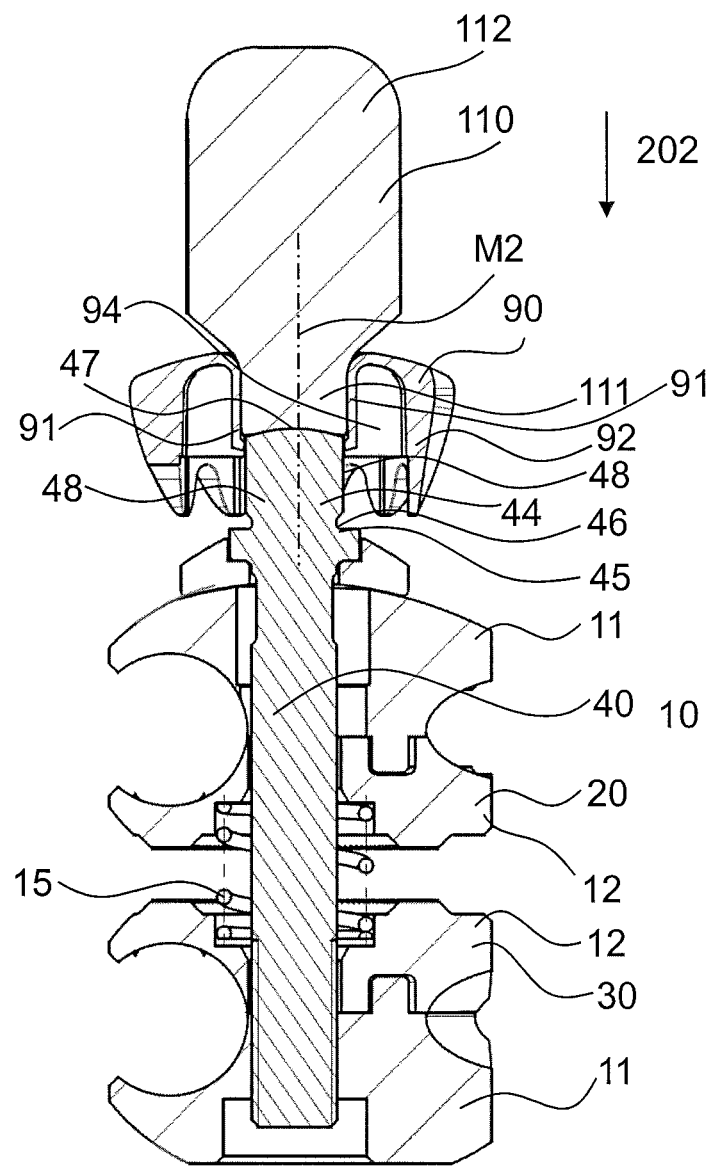
FIG. 10 shows a cross-sectional view of the arrangement of FIG. 7 during assembly.

FIG. 10 shows the actuation element 90 in the mounting state in which the actuation element 90 will be moved towards the fixation clamp 10 in direction of arrow 202, wherein the head portion 44 of the locking element 40 extends into the interior space 94 between the latching elements 91. The latching element 91 is thereby in contact with the side surface 48 of the locking element 40 and therefore it is possible to move the actuation element 90 with respect to the locking element 40.

Figure 11:
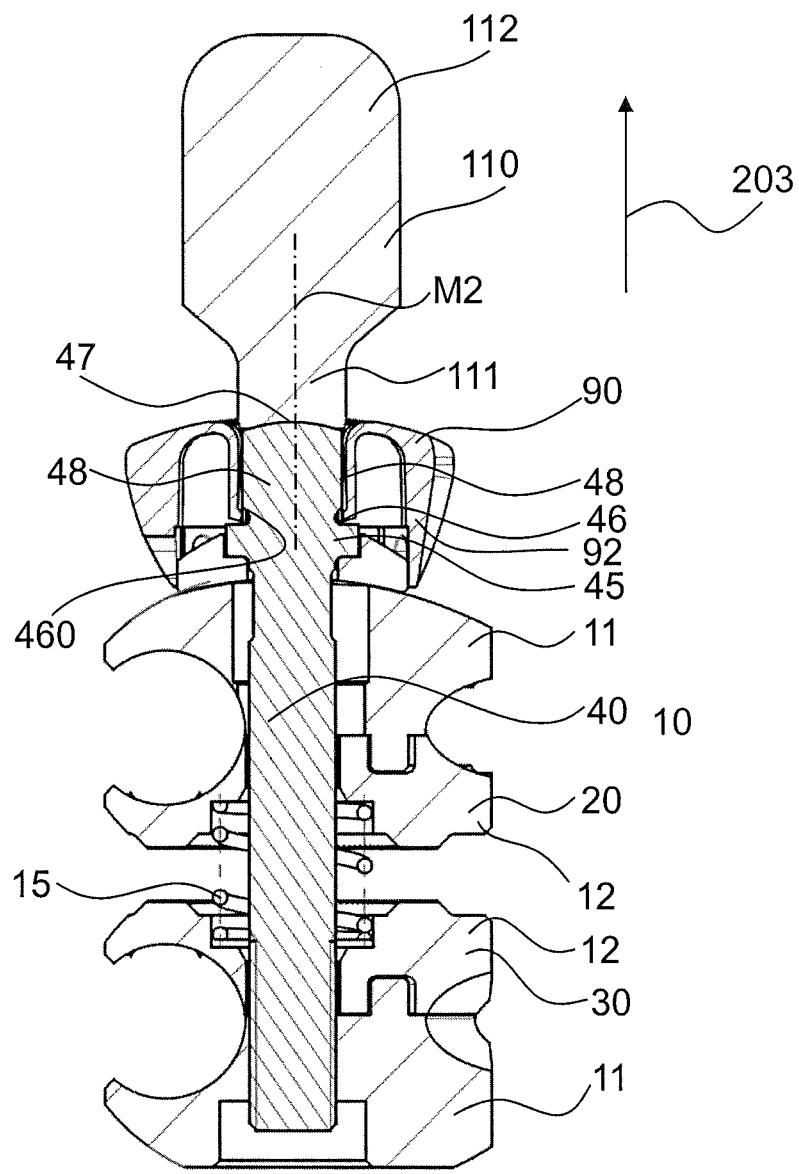
FIG. 11 shows a cross-sectional view of the arrangement of FIG. 7 after assembly.

FIG. 11 shows the end position of the actuation element 90 with regard to the locking element 40. Thereby the actuation element 90 is in a position in which the engaging elements 97 are able to engage into the recesses 46 of the locking element 40. Once the actuation element 90 has reached its end position as shown in FIG. 11 the resilient latching elements 91 will move to their originating position and engage into the recesses 46. In this state the fixation clamp 10 is ready to be used by a user in a operating theatre during a surgery.

Once the user has pretensioned or pretightened the fixation clamp 10 by means of the actuation element 90, the actuation element 90 is detachable from the locking element 10. In order to enhance this detaching process the recesses 46 comprise chamfered edges 460 which are inclined towards the middle axis M1 such that the latching elements 91 will be moved away from the middle axis M2 upon a displacement of the actuation element 90 relative to the recess 46. Afterwards with increasing distance between the fixation clamp 10 and the actuation element 90 the latching elements 91 are in contact with the side surfaces 48 of the locking element 40 and slides on these surfaces. During detaching the actuation element 90 the user has to apply a force in direction of arrow 203 as shown in FIG. 11.

Once the actuation element 90 is completely detached from the locking element 40, the latching elements 91 will move back to their origin position due to the resilient structure. Thereby the abutment surfaces 96 are arranged such that the locking element 40 abuts with its top surface 47 on the abutment surfaces 96. Hence it is not possible to remount the actuation element 90.

The actuation element 90 is preferably made out of plastic material, in particular out of a thermoplastic.

The actuation element 90 has the following advantages: First of all it is possible to pretighten the fixation clamp 10 by hand without the aid of an additional tool. Furthermore the user is able to recognize, if the fixation clamp is ready for use when the actuation element 90 is still mounted or, if the fixation clamp has been used in which case the actuation element is removed. Furthermore false use is prevented due to the fact that the actuation element 90 cannot be remounted without the aid of a respective tool.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixation clamp for use in an external fixation system for holding bone fragments adjacent to each other with the help of fixation elements, said clamp comprising:
   at least one clamping assembly having at least one reception to accommodate a fixation element along the longitudinal axis of the reception and at least one locking element extending through the clamping assembly, the locking element having a middle axis and a drive portion, the locking element drive portion having an outer surface spaced a distance outwardly from the middle axis, the locking element is capable of providing a clamping force to clamp the fixation element upon tensioning the locking element and,
   an actuation element having at least one elastically deflectable latching element, the at least one latching element in an undeflected state extends inwardly towards the locking element middle axis a distance greater than the distance from the middle axis to the outer surface of the locking element drive portion, the actuation element can be connected with the locking element when the at least one latching element is deflected outwardly from the middle axis a distance greater than the distance from the middle axis to the outer surface of the locking element drive portion such that the locking element is actuateable by means of the actuation element, wherein the actuation element is designed such that it is detachable from the locking element after use and that remounting onto the locking element is prevented by the at least one latching element in an undeflected state after having detached the actuation element from the locking element, wherein the locking element comprises at least one recess in which the at least one latching element engages when the actuation element is mounted in the locking element drive portion after being deflected outwardly from the middle axis.

2. The fixation clamp according to claim 1, wherein the actuation element is prevented from re-use by the engagement of the at least one latching element in the undeflected state and an upwardly facing surface of the locking element drive portion of the locking element.

3. The fixation clamp according to claim 1, wherein the actuation element is designed as a disposable element.

4. The fixation clamp according to claim 1, wherein the at least one elastically deflectable latching element comprises at least two elastically deflectable latching elements which are arranged diagonally across from one another with respect to the locking element drive portion.

5. The fixation clamp according to claim 1, wherein the at least one elastically deflectable latching element comprises first and second pair of elastically deflectable latching elements, the first and second pair are respectively arranged diagonally across from one another with respect to the locking element drive portion.

6. The fixation clamp according to claim 1, wherein the actuation element comprises a central opening extending along a central axis and said at least one elastically deflectable latching elements extending in a direction of said central opening and towards said central axis in an undeflected state.

7. The fixation clamp according to claim 6, wherein the actuation element comprises a substantially cylindrical sidewall providing an interior space and a frontwall extending from said sidewall into the interior space, whereby the frontwall comprises said central opening along which said at least one elastically deflectable latching element extends.

8. The fixation clamp according to claim 7, wherein the at least one elastically deflectable latching element is provided as an elastic or a resilient beam element having a first end which is in contact with the sidewall or the frontwall of the actuation element and a second end which is provided as a free end.

9. The fixation clamp according to claim 8, wherein the at least one elastically deflectable latching element comprises an engaging element which engages with the locking element in said at least one recess.

10. The fixation clamp according to claim 9, wherein the engaging element is arranged in the vicinity of the free end of the at least one elastically deflectable latching element.

11. The fixation clamp according to claim 1, wherein the at least one recess in which the at least one elastically deflectable latching element engages extends into the locking element drive portion of the locking element towards the middle axis.

12. The fixation clamp according to claim 1, wherein the locking element drive portion of the locking element comprises a top surface extending substantially perpendicular to the middle axis of the locking element and a plurality of outer side surfaces extending substantially parallel to said middle axis, wherein the at least one recess extends into a corresponding outer side surface.

13. The fixation clamp according to claim 12, wherein the at least one elastically deflectable latching element comprises an abutment surface which is arranged such that during remounting of the actuation element, the abutment surface abuts against the locking element drive portion.

14. The fixation clamp according to claim 12, wherein the at least one elastically deflectable latching element comprises an abutment surface which is arranged such that it abuts against a surface of the locking element during remounting of the actuation element against the locking element.

15. The fixation clamp according to claim 1, wherein the at least one elastically deflectable latching element is deflected outwardly from the middle axis by means of a mounting tool from a blocking position to a mounting position, wherein in said blocking position the at least one latching element is positioned such that it abuts onto a top portion of the locking element in order to prevent remounting and wherein in said mounting position the at least one latching element is positioned such that the actuation element is moveable with respect to an outer surface of the locking element drive portion.

16. The fixation clamp according to claim 15, wherein said mounting tool deforms said at least one elastically deflectable latching element away from the middle axis such that the clearance between the at least one deflectable latching element will be enlarged in order to receive the locking element drive portion.

17. The fixation clamp according to claim 1, wherein the actuation element comprises an outer surface having friction enhancing elements for increasing friction between a user's hand and the actuation element.

18. A fixation clamp for use in an external fixation system for holding bone fragments adjacent to each other with the help of fixation elements, said clamp comprising:
   a reception opening to accommodate a fixation element along a longitudinal axis of the reception opening and at least one locking element extending through the clamping assembly, the locking element is capable of providing a clamping force to clamp the fixation element upon tensioning the locking element, and
   an actuation element which is in connection with the locking element such that the locking element is actuateable by means of the actuation element wherein the actuation element comprises at least one elastically deflectable latching element having an abutment surface,
   wherein said at least one elastically deflectable latching element engages with the locking element and is deflectable away from a middle axis of the locking element such that the actuation element is detachable from the locking element after use, and
   wherein the at least one elastically deflectable latching element abutment surface extends in an undeflected state towards the middle axis of the locking element a distance so that it abuts against an outwardly facing surface of the locking element to prevent mounting the actuation element onto the locking element and wherein the locking element comprises a recess in which the at least one elastically deflectable latching element engages when the actuation element is mounted on the locking element after the latching element has been deflected away from the middle axis.

19. The fixation clamp according to claim 18, wherein the actuation element comprises at least two elastically deflectable latching elements which are arranged diagonally with respect to the locking element from each other.

20. The fixation clamp according to claim 19, wherein the actuation element comprises a substantially cylindrical outer sidewall providing an interior space defining a frontwall extending from said sidewall into the interior space, whereby the frontwall comprises said central opening along which said latching element extends.

21. The fixation clamp according to claim 20, wherein the elastically deflectable latching element is provided as an elastic or a resilient beam element having a first end which is in contact with the sidewall or the frontwall and a second end which is provided as a free end.

22. The fixation clamp according to claim 21, wherein the at least one elastically deflectable latching element abutment surface is arranged in the vicinity of said free end.

23. The fixation clamp according to claim 18, wherein the actuation element comprises a central opening extending along a central axis thereof and said at least one latching element extends into said central opening toward the central axis.

24. The fixation clamp according to claim 18, wherein the locking element recess in which the at least one elastically deflectable latching element engages extends into a head portion of the locking element.

25. The fixation clamp according to claim 18, wherein the head portion of the locking element comprises a top surface extending substantially perpendicular to the middle axis of the locking element and a plurality of side surfaces extending substantially parallel to said middle axis, wherein the locking element recess extends into one of said side surfaces towards of the middle axis.

26. The fixation clamp according to claim 25, wherein the at least one elastically deflectable latching element abutment surface is arranged such that it abuts against the top surface of the locking element when mounting the actuation element.

27. The fixation clamp according to claim 26, wherein said at least one elastically deflectable latching element comprises a plurality of elastically deflectable latching elements and wherein said mounting tool deforms said plurality of elastically deflectable latching elements away from the middle axis such that the clearance between the latching elements will be enlarged in order to receive the locking element.

28. A fixation clamp for use in an external fixation system comprising:
   a clamping assembly comprising first and second jaw members each having a central bore therethrough and a locking element having a drive head and a shaft portion extending along a middle axis mounted in the central through bores of the first and second jaw members, the locking element having a recessed groove extending around an outer circumference thereof between the drive head and the shaft portion;
   an actuator element having a body with a central opening mounted on the drive head of the locking element, the actuation element having a least one elastically deflectable latch element mounted in the central opening, the latch element having a leg portion having a first end coupled to the actuation element body and a second free end capable of deflecting from a non-deflected position away from the middle axis a distance sufficient to engage the groove in the locking element, the latch element leg portion deflectable away from the middle axis a distance to allow the free end to disengage from the groove on the locking element.

* * * * *